United States Patent
Gauthier et al.

(10) Patent No.: US 12,369,928 B2
(45) Date of Patent: *Jul. 29, 2025

(54) METHOD OF FORMING A REUSABLE SURGICAL IMPLEMENT

(71) Applicant: Gauthier Biomedical, Inc., Grafton, WI (US)

(72) Inventors: Michael T. Gauthier, Grafton, WI (US); Kenneth A. Roggow, Milwaukee, WI (US)

(73) Assignee: Gauthier Biomedical, Inc, Grafton, WI (US)

( * ) Notice: Subject to any disclaimer, the term of this patent is extended or adjusted under 35 U.S.C. 154(b) by 979 days.

This patent is subject to a terminal disclaimer.

(21) Appl. No.: 16/750,239

(22) Filed: Jan. 23, 2020

(65) Prior Publication Data

US 2020/0155171 A1 May 21, 2020

Related U.S. Application Data

(62) Division of application No. 14/713,367, filed on May 15, 2015, now Pat. No. 10,588,642.

(Continued)

(51) Int. Cl.
*B29C 45/14* (2006.01)
*A61B 17/00* (2006.01)
(Continued)

(52) U.S. Cl.
CPC .......... *A61B 17/1631* (2013.01); *A61B 17/00* (2013.01); *A61B 17/1642* (2013.01);
(Continued)

(58) Field of Classification Search
CPC .............. B29C 45/14; B29C 45/14336; B29C 45/14475; B29C 45/1671
See application file for complete search history.

(56) References Cited

U.S. PATENT DOCUMENTS

| 1,813,797 A | 7/1931 | William |
| 1,831,752 A | 11/1931 | Reinold |

(Continued)

FOREIGN PATENT DOCUMENTS

| CN | 2494172 | 6/2002 |
| CN | 1357444 | 7/2002 |

(Continued)

OTHER PUBLICATIONS

Hoxha et al., "Field-improvised war surgery in Kosovo; use of kitchen utensils as surgical instruments", Jun. 2008, Military Medicine, vol. 173, pp. 529-533.

(Continued)

*Primary Examiner* — Edmund H Lee
(74) *Attorney, Agent, or Firm* — Boyle Frederickson S.C

(57) ABSTRACT

A reusable surgical implement is provided that is formed of a core positioned within an enclosure. The core is formed of a suitable rigid, and optionally flexible material to enable the implant to conform to the desired use for the implement in a surgical procedure. The material forming the enclosure is also stretchable and flexible to accommodate the configuration and/or any flexing of the core, and is biologically inert to enable the implant to be sterilized after use for use in subsequent surgical procedures while protecting the material forming the core. The enclosure can be molded around the core in separate portions or components using multiple molding steps to form an enclosure with the desired attributes.

13 Claims, 2 Drawing Sheets

Related U.S. Application Data

(60) Provisional application No. 61/993,383, filed on May 15, 2014.

(51) Int. Cl.

| | | |
|---|---|---|
| *A61B 17/16* | (2006.01) | |
| *A61B 17/88* | (2006.01) | |
| *B29C 45/16* | (2006.01) | |
| *B32B 3/02* | (2006.01) | |
| *A61B 17/70* | (2006.01) | |
| *A61B 90/00* | (2016.01) | |
| *B29C 45/26* | (2006.01) | |
| *B29K 83/00* | (2006.01) | |
| *B29K 705/08* | (2006.01) | |
| *B29L 9/00* | (2006.01) | |
| *B29L 31/00* | (2006.01) | |
| *B29L 31/06* | (2006.01) | |
| *B32B 1/00* | (2006.01) | |
| *B32B 3/26* | (2006.01) | |
| *B32B 3/30* | (2006.01) | |
| *B32B 7/02* | (2019.01) | |
| *B32B 7/04* | (2019.01) | |
| *B32B 15/06* | (2006.01) | |

(52) U.S. Cl.
CPC ........ *A61B 17/88* (2013.01); *B29C 45/14008* (2013.01); *B29C 45/14336* (2013.01); *B29C 45/1671* (2013.01); *B32B 3/02* (2013.01); A61B 2017/00526 (2013.01); A61B 2017/00831 (2013.01); A61B 2017/00862 (2013.01); A61B 2017/00867 (2013.01); A61B 2017/00946 (2013.01); A61B 2017/00955 (2013.01); A61B 2017/00964 (2013.01); A61B 17/164 (2013.01); A61B 17/1671 (2013.01); A61B 17/7002 (2013.01); A61B 17/7029 (2013.01); A61B 17/7031 (2013.01); A61B 2090/0813 (2016.02); B29C 2045/14139 (2013.01); B29C 45/14549 (2013.01); B29C 45/14598 (2013.01); B29C 2045/1486 (2013.01); B29C 45/1642 (2013.01); B29C 45/1679 (2013.01); B29C 45/261 (2013.01); B29K 2083/00 (2013.01); B29K 2083/005 (2013.01); B29K 2705/08 (2013.01); B29L 2009/00 (2013.01); B29L 2009/003 (2013.01); B29L 2031/06 (2013.01); B29L 2031/75 (2013.01); B29L 2031/7546 (2013.01); *B32B 1/00* (2013.01); *B32B 3/263* (2013.01); *B32B 3/30* (2013.01); *B32B 7/02* (2013.01); *B32B 7/04* (2013.01); *B32B 15/06* (2013.01); *B32B 2311/00* (2013.01); *B32B 2311/005* (2013.01); *B32B 2383/00* (2013.01); *B32B 2535/00* (2013.01)

(56) References Cited

U.S. PATENT DOCUMENTS

| | | | |
|---|---|---|---|
| 2,062,880 | A | 12/1936 | Hansen |
| 2,125,783 | A | 8/1938 | Heeman |
| 2,207,269 | A | 7/1940 | Schiff |
| 2,256,769 | A | 9/1941 | Amrine |
| 2,358,259 | A * | 9/1944 | Siedschlag ............. B29C 70/70 425/468 |
| 3,259,680 | A | 7/1966 | Schelke |
| 3,913,586 | A | 10/1975 | Baumgarten |
| 4,117,791 | A | 10/1978 | Current |
| 4,147,443 | A | 4/1979 | Skobel |
| 4,170,990 | A | 10/1979 | Baumgart |
| 4,318,879 | A | 3/1982 | Gartner |
| 4,340,990 | A | 7/1982 | Seynhaeve |
| 4,448,741 | A * | 5/1984 | Schad ................ B29D 12/02 264/254 |
| 4,464,797 | A * | 8/1984 | Glassman ......... A41D 13/1153 128/201.12 |
| 4,469,483 | A | 9/1984 | Becker |
| 4,535,014 | A | 8/1985 | Wright |
| 4,662,404 | A | 5/1987 | LaVeen |
| 4,690,175 | A | 9/1987 | Ouchi |
| 4,706,659 | A | 11/1987 | Matthews |
| 4,739,536 | A | 4/1988 | Bandera |
| 4,750,877 | A | 6/1988 | McFarlane |
| 4,751,922 | A | 6/1988 | DiPietropolo |
| 4,799,474 | A | 1/1989 | Ueda |
| 4,867,174 | A | 9/1989 | Skribiski |
| 4,882,867 | A | 11/1989 | Linden |
| 4,919,133 | A | 4/1990 | Chiang |
| 4,934,024 | A | 6/1990 | Sexton |
| 4,955,889 | A | 9/1990 | Van Gent |
| 4,959,067 | A | 9/1990 | Muller |
| 4,983,168 | A | 1/1991 | Moorehead |
| 5,027,511 | A | 7/1991 | Miller |
| 5,069,226 | A | 12/1991 | Yamauchi |
| 5,089,201 | A | 2/1992 | Takahashi |
| 5,095,915 | A | 3/1992 | Engelson |
| 5,163,431 | A | 11/1992 | Griep |
| 5,222,949 | A | 6/1993 | Kaldany |
| 5,230,348 | A | 7/1993 | Ishibe |
| 5,334,168 | A | 8/1994 | Hemmer |
| 5,385,152 | A | 1/1995 | Abele |
| 5,424,787 | A * | 6/1995 | Zegarelli ................ A61F 9/029 351/158 |
| 5,433,200 | A | 7/1995 | Fleischhacker, Jr. |
| 5,498,158 | A | 3/1996 | Wong |
| 5,499,984 | A | 3/1996 | Steiner |
| 5,533,985 | A | 7/1996 | Wang |
| 5,538,512 | A | 7/1996 | Zenzon |
| 5,569,218 | A | 10/1996 | Berg |
| 5,573,529 | A | 11/1996 | Haak |
| 5,601,003 | A | 2/1997 | Amtenbrink |
| 5,662,621 | A | 9/1997 | Lafontaine |
| 5,769,506 | A | 6/1998 | Boucherie |
| 5,772,609 | A | 6/1998 | Nguyen |
| 5,799,369 | A | 9/1998 | Schulein |
| 5,816,806 | A | 10/1998 | Herbst |
| 5,816,923 | A | 10/1998 | Milo |
| 5,911,715 | A | 6/1999 | Berg |
| 5,921,978 | A | 7/1999 | Thompson |
| 5,956,799 | A | 9/1999 | Panaccione |
| 5,964,770 | A | 10/1999 | Flomenblit |
| 6,036,682 | A | 3/2000 | Lange |
| 6,094,781 | A | 8/2000 | Jansson |
| 6,199,460 | B1 | 3/2001 | Lo |
| 6,221,077 | B1 | 4/2001 | Rinner |
| 6,340,441 | B1 | 1/2002 | Meyer |
| 6,367,125 | B1 | 4/2002 | Lin |
| 6,368,536 | B1 * | 4/2002 | Hoepfl ............... B29C 45/1671 264/250 |
| 6,402,706 | B2 | 6/2002 | Richardson |
| 6,405,619 | B1 | 6/2002 | Lamond |
| 6,494,847 | B1 | 12/2002 | Richardson |
| 6,494,894 | B2 | 12/2002 | Mirarchi |
| 6,524,301 | B1 | 2/2003 | Wilson |
| 6,556,873 | B1 | 4/2003 | Smits |
| 6,591,472 | B1 | 7/2003 | Noone |
| 6,648,024 | B2 | 11/2003 | Wang |
| 6,749,790 | B1 | 6/2004 | Lieser |
| 6,779,937 | B1 | 8/2004 | Lombardi |
| 6,887,417 | B1 | 5/2005 | Gawreluk |
| 6,915,570 | B1 | 7/2005 | Ohgoshi |
| 7,097,624 | B2 * | 8/2006 | Campion ............... A61M 25/09 600/585 |
| 7,651,578 | B2 | 1/2010 | Sharrow |
| 7,780,611 | B2 | 8/2010 | Griego |
| 7,947,206 | B2 * | 5/2011 | Chen ................ A63B 69/3632 264/249 |
| 8,641,955 | B2 * | 2/2014 | Gauthier ............ B29C 45/2675 264/247 |

(56) References Cited

U.S. PATENT DOCUMENTS

| | | | |
|---|---|---|---|
| 9,050,062 B1 | 6/2015 | Gauthier | |
| 9,943,988 B1* | 4/2018 | Gauthier | A61B 17/88 |
| 2001/0041881 A1 | 11/2001 | Sarge | |
| 2002/0013511 A1 | 1/2002 | Ailinger | |
| 2002/0058928 A1 | 5/2002 | Antonio | |
| 2002/0107088 A1 | 8/2002 | Lamkin | |
| 2002/0126255 A1* | 9/2002 | Chang | G02B 7/002 |
| | | | 351/158 |
| 2002/0128658 A1 | 9/2002 | White | |
| 2002/0165549 A1 | 11/2002 | Owusu-Akyaw | |
| 2002/0171208 A1 | 11/2002 | Lechot | |
| 2002/0190430 A1 | 12/2002 | Fujiwara | |
| 2003/0009713 A1 | 5/2003 | Green | |
| 2003/0126750 A1 | 7/2003 | Spinelli | |
| 2003/0022929 A1 | 12/2003 | Iwami | |
| 2004/0097831 A1 | 5/2004 | Bourne | |
| 2004/0098006 A1 | 5/2004 | Nakanishi | |
| 2004/0105069 A1 | 6/2004 | Fecteau | |
| 2004/0134028 A1 | 7/2004 | Chen | |
| 2004/0167437 A1 | 8/2004 | Sharrow | |
| 2004/0193104 A1 | 9/2004 | Jervis | |
| 2004/0243102 A1 | 12/2004 | Berg | |
| 2005/0004556 A1 | 1/2005 | Pursley | |
| 2005/0049623 A1 | 3/2005 | Moore | |
| 2005/0054953 A1 | 3/2005 | Ryan | |
| 2005/0113686 A1 | 5/2005 | Peckham | |
| 2005/0124991 A1 | 6/2005 | Jahng | |
| 2005/0137600 A1 | 6/2005 | Jacobs | |
| 2005/0253301 A1 | 11/2005 | Kraenzle | |
| 2006/0004371 A1 | 1/2006 | Willlams | |
| 2006/0009140 A1 | 1/2006 | Sommers | |
| 2006/0063130 A1 | 3/2006 | Hayman | |
| 2006/0084032 A1 | 4/2006 | Tipton | |
| 2006/0100687 A1 | 5/2006 | Fahey | |
| 2006/0110704 A1 | 5/2006 | Bills | |
| 2006/0189897 A1 | 8/2006 | Poncet | |
| 2006/0199994 A1 | 9/2006 | Inman | |
| 2006/0247638 A1 | 11/2006 | Trieu | |
| 2006/0264935 A1 | 11/2006 | White | |
| 2007/0003903 A1 | 1/2007 | Meuchel | |
| 2007/0049937 A1 | 3/2007 | Matthis | |
| 2007/0073312 A1 | 3/2007 | Mykleby | |
| 2007/0123826 A1 | 5/2007 | Opie | |
| 2007/0153229 A1 | 7/2007 | Yasuhara | |
| 2007/0161427 A1 | 7/2007 | White | |
| 2007/0191841 A1 | 8/2007 | Justis | |
| 2007/0299366 A1 | 12/2007 | Sharrow | |
| 2008/0125238 A1 | 5/2008 | Chen | |
| 2008/0125777 A1 | 5/2008 | Veldman | |
| 2008/0140022 A1 | 6/2008 | Pond | |
| 2008/0146967 A1 | 6/2008 | Richardson | |
| 2008/0177388 A1 | 7/2008 | Patterson | |
| 2008/0234711 A1 | 9/2008 | Houser | |
| 2008/0243126 A1 | 10/2008 | Gutierrez | |
| 2008/0255664 A1 | 10/2008 | Hogendijk | |
| 2008/0287952 A1 | 11/2008 | Mcminn | |
| 2008/0290104 A1 | 11/2008 | Ng | |
| 2008/0312597 A1* | 12/2008 | Uihlein | A61M 25/09 |
| | | | 604/164.13 |
| 2008/0312654 A1 | 12/2008 | Weatherdon | |
| 2008/0319486 A1 | 12/2008 | Hestad | |
| 2009/0054932 A1 | 2/2009 | Butler | |
| 2009/0088750 A1 | 4/2009 | Hushka | |
| 2009/0088782 A1 | 4/2009 | Moumene | |
| 2009/0112066 A1 | 4/2009 | Yago | |
| 2009/0112127 A1 | 4/2009 | Keating | |
| 2009/0161063 A1* | 6/2009 | Parent | G02C 5/18 |
| | | | 351/114 |
| 2009/0221935 A1 | 9/2009 | Murayama | |
| 2009/0248080 A1 | 10/2009 | Wilcox | |
| 2009/0259257 A1 | 10/2009 | Prevost | |
| 2009/0270922 A1 | 10/2009 | Biedermann | |
| 2010/0005630 A1 | 1/2010 | Gitman | |
| 2010/0030256 A1 | 2/2010 | Dubrul | |
| 2010/0063544 A1 | 3/2010 | Butler | |
| 2010/0063548 A1 | 3/2010 | Wang | |
| 2010/0102479 A1 | 4/2010 | Wallis | |
| 2010/0256601 A1 | 10/2010 | Lippert | |
| 2010/0256603 A1 | 10/2010 | Lippert | |
| 2010/0256605 A1 | 10/2010 | Lippert | |
| 2010/0324577 A1 | 12/2010 | Dunn | |
| 2011/0071570 A1 | 3/2011 | Trieu | |
| 2011/0138975 A1 | 6/2011 | Holm | |
| 2011/0152937 A1 | 6/2011 | Trieu | |
| 2011/0168419 A1 | 7/2011 | Reynolds | |
| 2011/0218538 A1 | 9/2011 | Sherman | |
| 2011/0257685 A1 | 10/2011 | Hay | |
| 2012/0041305 A1* | 2/2012 | Grissom | A61B 5/415 |
| | | | 600/431 |
| 2012/0041425 A1 | 2/2012 | Tsunematsu | |
| 2012/0253348 A1 | 10/2012 | Arlettaz | |
| 2012/0290013 A1 | 11/2012 | Simonson | |
| 2013/0066164 A1 | 3/2013 | Nakamura | |
| 2013/0233863 A1 | 9/2013 | Lapine | |
| 2013/0253481 A1 | 9/2013 | Dewaele | |
| 2015/0042945 A1* | 2/2015 | Curley | G02C 9/00 |
| | | | 351/57 |
| 2015/0121708 A1 | 5/2015 | Holm | |
| 2015/0257800 A1 | 9/2015 | Harshman | |
| 2015/0313755 A1 | 11/2015 | Schaller | |
| 2016/0023504 A1 | 1/2016 | Shapiro | |
| 2016/0184555 A1 | 6/2016 | Ishikawa | |
| 2018/0177532 A1 | 6/2018 | Gauthier | |
| 2019/0045782 A1* | 2/2019 | Edye | G02C 11/00 |

FOREIGN PATENT DOCUMENTS

| | | |
|---|---|---|
| CN | 200995040 | 12/2007 |
| CN | 101954810 | 1/2011 |
| CN | 102188280 | 9/2011 |
| CN | 102717478 | 10/2012 |
| DE | 7914109 | 5/1979 |
| DE | 102006054477 | 5/2008 |
| EP | 0904921 | 3/1999 |
| EP | 1561548 | 8/2005 |
| FR | 2509986 | 1/1983 |
| FR | 2612305 | 9/1988 |
| GB | 501019 | 2/1939 |
| GB | 2359268 | 8/2001 |
| GB | 2464751 | 5/2010 |
| GB | 2493147 | 1/2013 |
| JP | 01086908 | 3/1989 |
| JP | 01115510 | 8/1989 |
| JP | 2003191681 | 7/2003 |
| JP | 2003319955 | * 11/2003 |
| JP | 2007037777 | 2/2007 |
| KR | 20100071574 | 6/2010 |
| KR | 20100071575 | 6/2010 |
| WO | 2008022524 | 2/2008 |
| WO | 2011066231 | 6/2011 |

OTHER PUBLICATIONS

Silicone Handles, Gauthier Medical, Feb. 2012.
Silicone Rod Templates, Gauthier Medical, Mar. 2012.

* cited by examiner

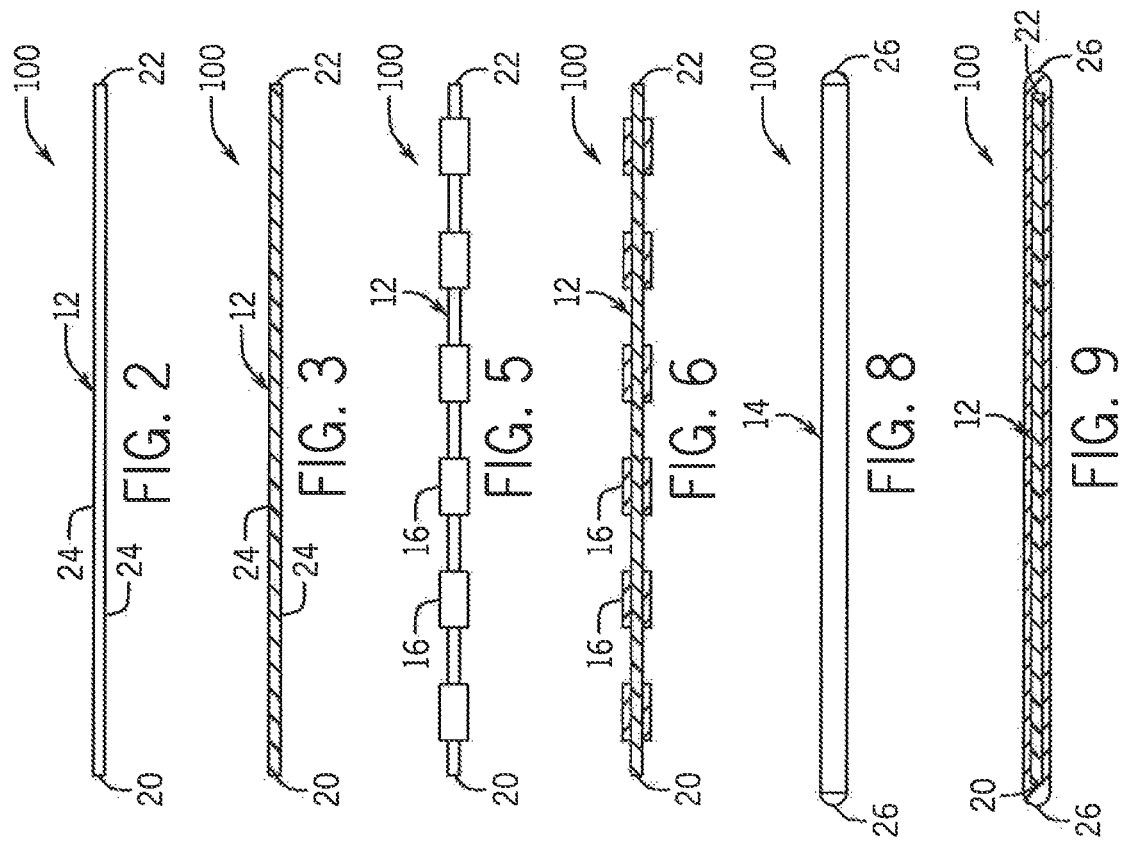
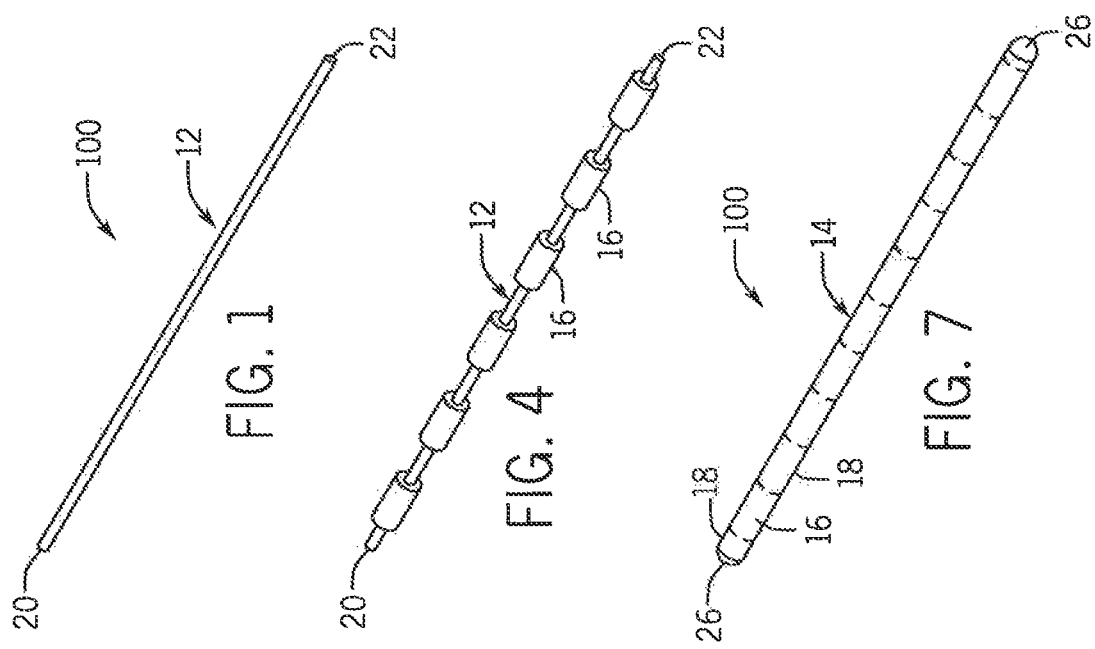

METHOD OF FORMING A REUSABLE SURGICAL IMPLEMENT

CROSS-REFERENCE TO RELATED APPLICATIONS

This application is a division of U.S. application Ser. No. 14/713,367, filed May 15, 2015, now U.S. Pat. No. 10,588,642, which claims priority from U.S. Provisional Patent Application Ser. No. 61/993,383, filed on May 15, 2014, the entirety of which is expressly incorporated herein by reference.

FIELD OF THE INVENTION

The present invention relates generally to items used in surgical procedures, and more particularly to a process for molding exterior coatings on those items and the items formed by the molding process.

BACKGROUND OF THE INVENTION

There are many types of devices that are used in surgical procedures. The devices enable a physician to perform the multitude of tasks required to successfully complete the procedure. Oftentimes, the procedure that the physician needs to perform requires the use of items, implements or other tools that require a certain amount of rigidity in the tool in order for the tool to effective in its particular use in the procedure. As such, many of these items or tools are formed of a generally rigid material, such as a metal, that provides the desired amount of rigidity.

However, with these tools formed at least partially of metal, the nature of the metal creates problems with regard to the re-use of the tool. The reason for this is that the metal, as well as any coating applied to the exterior of the metal, such as an anodized coating which is necessary for implements that are formed of titanium, must be sterilized after each use. With certain metals and coatings, the sterilization process can be problematic, as the metals and/or coating can become brittle or otherwise damaged upon sterilization after an initial use. Any damage done to the metal and/or coating can cause issues with the stability or integrity of the implement during subsequent uses which consequently can endanger the patient.

Thus, it is desirable to develop implements that are formed of metal and a material that enables the implement/tool incorporating the metal to be sterilized and reused in multiple procedures without detrimentally affecting the tool and/or the metal component(s) of the tool.

SUMMARY OF THE INVENTION

Briefly described, one aspect of the present disclosure provides an implement or tool formed of a substantially rigid, but optionally somewhat flexible core material that is enclosed within an inert material. The inert material provide a protective barrier around the core material and is capable of being sterilized after use without degrading the protective properties of the inert material to enable the implement to be reused. The inert material is molded over the core material to conform to the shape of the actual implement to provide the appropriate size and shape for the implement or tool when used by a physician in the procedure. Once used, the implement can be removed and subsequently sterilized, such as in an autoclave, for additional uses.

According to another aspect of the present disclosure, the inert material is flexible and stretchable to accommodate any required flexibility of the core material while maintaining the core enclosed within the inert material. Thus, the implement can be bent in order to accurately conform to the proper location and configuration of for the implement when positioned within the body of the patient during the procedure and the inert material will maintain its conformance with the shape of the core.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings:

FIG. 1 is an isometric view of one embodiment of an implement core constructed according to the present disclosure;

FIG. 2 is a side elevation view of the core of FIG. 1;

FIG. 3 is a cross-sectional view of the core of FIG. 2;

FIG. 4 is an isometric view of the core of FIG. 1 after a first molding step;

FIG. 5 is a side elevation view of the core of FIG. 4;

FIG. 6 is a cross-sectional view of the core of FIG. 5;

FIG. 7 is an isometric view of the core/implement of FIG. 1 after a second molding step;

FIG. 8 is a side elevation view of the core/implement of FIG. 7;

FIG. 9 is a cross-sectional view of the core/implement of FIG. 8;

DETAILED DESCRIPTION OF THE INVENTION

Figure 11:
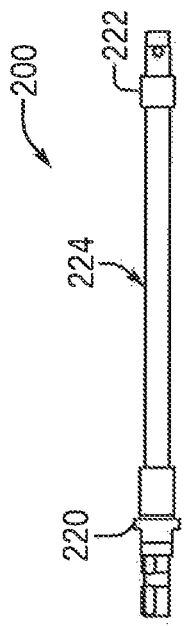
FIG. 11 is a side elevation view of the implement core of FIG. 10.

Referring now in detail to the drawing figures, wherein like reference numerals represent like parts throughout the several views, one exemplary embodiment of an implement constructed according to the present disclosure is illustrated generally at 100 in FIG. 7. As best shown in FIGS. 1-9, the illustrated exemplary embodiment of the implement 100 is formed as a rod template having a central core 12 and an enclosure 14 disposed around the core 12 formed of a first component or portion(s) 16 and a second component or portion(s) 18. In the illustrated exemplary embodiment, the rod template 100 is formed to be generally straight, though other curved, looped or other configurations for the rod template 100 are also contemplated as being within the scope of the disclosure of the present invention.

Though any suitable shape for the core 12 can be utilized, in the illustrated embodiment the core 12 is formed with a generally flat rectangular or cylindrical cross-sectional shape with a first end 20 and a second end 22 joined by opposed sides 24, though any suitable cross-sectional shape can be utilized to impart the desired amount of flexibility to the core 12. The core 12 is shaped in any suitable machine and/or process to provide the desired shape for the core 12, which may include apertures or other features therein, as desired.

The material forming the core 12 is selected to be a generally rigid, but flexible material that can be altered in shape by applying a physical force to the core 12. Once the force is removed, the core 12 remains in the shape to which it was altered by the applied force. In one exemplary embodiment of the core 12, the core 12 is formed of a shape memory material, such as a shape memory metal alloy, including the materials marketed under the trade name Nitinol® by Nitinol Devices & Components, Inc. of Fremont, California.

The enclosure 14 is disposed around the core 12 and each portion 16 and 18 joined together to form the enclosure 14 is formed of a biologically inert and flexible material that can conform to the shape of the core 12 in any configuration for the core 12. In one embodiment, the material forming the portions 16 and 18 of the enclosure 14 is a silicone, such as a silicone rubber, including a high consistence rubber (HCR).

The portions 16 and 18 of the enclosure 14 are formed with any features (not shown) desired to enhance the utility of the implement 100 when utilized within the body of the patient. The features can include apertures 110, notches (not shown), raised or depressed tactile portions, or printed indicia, among others. The apertures can extend completely through the respective portions 16 and 18 without intersecting the core 12, thereby preserving the integrity of the enclosure 14 around the core 12. Further, the shape of the portions 16 and 18 forming the enclosure 14 can be shaped as desired. Also, the shape of the portions 16 and 18 can be selected independently of the shape of the core 12 to facilitate the operation or use of the implement 100, or to conform to the shape of the core 12, as desired.

In one embodiment, the implement 100 is formed by initially forming the core 12 of the desired material in any suitable manner, such as by extruding or molding the material into the desired shape for the core 12, as shown in FIGS. 1-3. The core 12 is then placed within a suitable mold (not shown) to enable the material selected to form the first portion 16 to be introduced into the mold containing the core 12 and form a portion of the enclosure 14 on or over the core 12 that contains the desired features within the portion 16. Any suitable molding process can be utilized to form the first portion 16 around the core 12, such as those shown in commonly owned U.S. Pat. No. 8,641,955 and its related applications, each of which are expressly incorporated by reference herein in their entirety. In the illustrated embodiment best shown in FIGS. 4-6, the first portion 16 constitutes a number of spaced sections 102 disposed along the length of the core 12.

Subsequently, the core 12 and the first portion 16 that has been molded onto or over the core 12 are removed or transferred from the first mold and placed within a separate or second mold (not shown) used to form the other of the second portion 18 on or over the core 12 in connection with the first portion 16 and with the desired features. The material selected to form the second portion 18 can be selected to be the same or different in one or more respects or attributes than the material used to form the first portion 16, in order to provide the desired attributes to the enclosure 14 and the implement 100, so long as the materials forming the first portion 16 and second portion 18 are capable of mating, co-mingling or otherwise joining to one another in the molding process used to form the enclosure 14 around the core 12, which can be the same or different that the process used to form the first section 16. Additionally, suitable materials can be applied to one or both of the portions 16 and/or 18 to properly affix the portions 16 and 18 to one another, either during molding of the portions 16 and 18 to one another, or when affixing pre-molded portions 16 and 18 to one another around the core 12.

In alternative exemplary embodiments, the portions 16 and 18 can be formed subsequently or simultaneously within a single mold in any suitable molding process. In the illustrated embodiment, the second portion 18 includes a number of spaced sections 104 disposed along the length of the core 12 and joining the sections 102 to form the enclosure 14. In this embodiment, as shown in FIGS. 7-9, the sections 102 and 104 form a seamless enclosure 14 around the core 12 complete with end caps 106 disposed over each end 20,22 of the core 12. The seamless enclosure 14 moves, stretches and/or flexes with the core 12 to retain the core 12 encased within the enclosure 14, such that the sterilization of the implement 100 does not contact the core 12.

Figure 13:
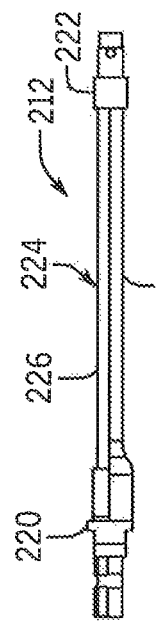
FIG. 13 is a side elevation view of the implement core of FIG. 12.
Figure 15:
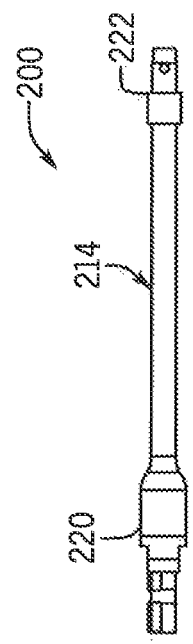
FIG. 15 is a side elevation view of the implement core of FIG. 14.
Figure 10:
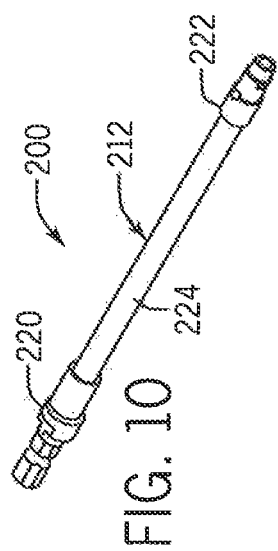
FIG. 10 is an isometric view of a second embodiment of an implement core constructed according to the present disclosure.
Figure 12:
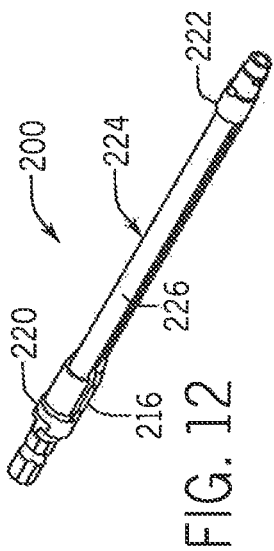
FIG. 12 is an isometric view of the implement core of FIG. 10 after a first molding step.
Figure 14:
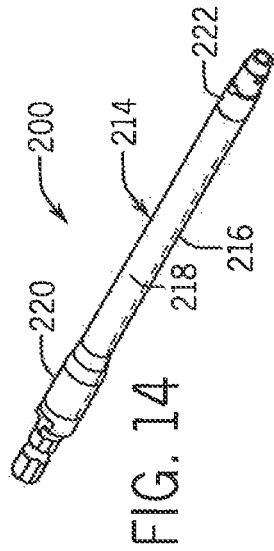
FIG. 14 is an isometric view of the implement core of FIG. 10 after a second molding step.

In a second embodiment of the implement 200 shown in FIGS. 10-15 illustrates the implement 200 as a flex driver. The implement 200 includes a suitably shaped core 212 with a pair of opposed ends 220 and 222. The ends 220 and 222 define a central section 224 therebetween, as best shown in FIGS. 10-13. In the embodiment shown in FIGS. 12 and 13, the first portion 216, which can be formed similarly to the first portion 16 in the prior embodiment, is molded onto the core 212 in a first mold (not shown) in a first molding step over at least approximately one half of the central section 224 in a suitable process, such as those cited as examples for the molding of the first portion 16 in the prior embodiment. In this process, however, the ends 220 and 222 can function as stops for the flow of the material forming the first portion 216 at each end 220 and 222.

Subsequently, the core 212 can be removed from the first mold for positioning in a second mold (not shown), or simply rotated within the first mold to expose the uncovered portion 226 of the central section 224 within the second mold. Once properly positioned, the second portion 218 can be formed over the uncovered section 226 to form the enclosure 214 over the central section 224 with the first portion 216 and without end caps, leaving the ends 220,222 exposed.

In alternative exemplary embodiments for either embodiment of the implement 100, 200, the process for molding the first portion 16,216 and/or second portion 18,218 can be performed in any number of separate molding steps in order to form the enclosure 14, 214 on the core 12,212 with the desired appearance, attributes or other characteristics with any desired number and/or types of different materials forming the portions 16,216 and/or 18,218.

Various other embodiments of the present disclosure are contemplated as being within the scope of the filed claims particularly pointing out and distinctly claiming the subject matter regarded as the invention.

The invention claimed is:
1. A method of forming a reusable surgical implement, the method comprising the steps of:
   a) forming a core;
   b) molding a first component of an enclosure entirely around the core; and c) molding a second component of the enclosure entirely around the core in engagement with the first component, wherein an exterior surface of the first component and an exterior surface of the second component form an exterior surface of the enclosure, and wherein the steps of molding the first component and molding the second component are performed in a single mold.

2. The method of claim 1 wherein the step of molding the first component comprises molding a number of first sections spaced from one another along the core.

3. The method of claim 1 wherein the step of molding the second component comprises molding a number of second sections spaced from one another along the core.

4. The method of claim 3 wherein the step of molding a number of second sections spaced from one another along the core further comprises mating, co-mingling or joining the second sections with the first sections to form a seamless enclosure.

5. The method of claim 1 wherein the core is formed of a shape memory material.

6. The method of claim 1 wherein the first and second components are silicone rubber.

7. The method of claim 1, wherein the steps of molding the first component and molding the second component are performed simultaneously.

8. A method of forming a reusable surgical implement, the method comprising the steps of:
   a) forming a core;
   b) forming an enclosure around the core, the step of forming the enclosure around the core consisting of the steps of:
      i) molding at least one first component of the enclosure around a circumference of the core; and
      ii) molding at least one second component of the enclosure around a circumference of the core in engagement with the at least one first component, wherein an exterior surface of the at least one first component and an exterior surface of the at least one second component form an exterior surface of the enclosure, wherein the reusable surgical implement is adapted to be placed at least partially within the body of a patient, and wherein the steps of molding the first component and molding the second component are performed simultaneously.

9. The method of claim 8 wherein the step of molding the at least one first component comprises molding a number of the at least one first components spaced from one another along the core.

10. The method of claim 8 wherein the step of molding the at least one second component comprises molding a number of the at least one second components spaced from one another along the core.

11. The method of claim 10 wherein the step of molding the number of at least one second components spaced from one another along the core further comprises mating, co-mingling or joining the number of at least one second components with the number of the at least one first components to form a seamless enclosure.

12. The method of claim 8 wherein the core is formed of a shape memory material.

13. The method of claim 8 wherein the at least one first components and the at least one second components are silicone rubber.

* * * * *